US008470018B2

(12) United States Patent
Hartley et al.

(10) Patent No.: US 8,470,018 B2
(45) Date of Patent: Jun. 25, 2013

(54) FENESTRATION FOR STENT GRAFT ARRANGEMENTS AND STENT GRAFT INCLUDING THE SAME

(75) Inventors: David Ernest Hartley, Wannanup (AU); Krasnodar Ivancev, London (GB)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/437,347

(22) Filed: Apr. 2, 2012

(65) Prior Publication Data

US 2012/0191180 A1    Jul. 26, 2012

Related U.S. Application Data

(62) Division of application No. 11/983,144, filed on Nov. 7, 2007, now Pat. No. 8,167,926.

(60) Provisional application No. 60/857,229, filed on Nov. 7, 2006.

(51) Int. Cl.
*A61F 2/06* (2006.01)

(52) U.S. Cl.
USPC .......................................... 623/1.13; 623/1.35

(58) Field of Classification Search
USPC ............................................. 623/1.13, 1.35
See application file for complete search history.

*Primary Examiner* — Thomas J Sweet
*Assistant Examiner* — Matthew Schall
(74) *Attorney, Agent, or Firm* — Richard J. Godlewski

(57) ABSTRACT

A fenestration (32) for a stent graft (30). The fenestration is an aperture in the biocompatible graft material and has at least one flap (38, 40) of a biocompatible graft material covering the aperture on the inside whereby the flap closes off the aperture but can be displaced to allow access through the fenestration. An array of such fenestrations may be placed on a stent graft to facilitate alignment of a branch vessel with a fenestration. A slip knot (46, 46) which can be released by forcing a dilator between the flaps can be used to hold the flaps together.

12 Claims, 7 Drawing Sheets

FENESTRATION FOR STENT GRAFT ARRANGEMENTS AND STENT GRAFT INCLUDING THE SAME

CROSS REFERENCE TO RELATED APPLICATIONS

This application is a divisional of U.S. patent application Ser. No. 11/983,144 filed on Nov. 7, 2007 entitled "Fenestration for Stent Graft Arrangements and Stent Graft Including the Same", the entire contents of which is incorporated herein by reference, and claims priority of provisional application Ser. No. 60/857,229, filed Nov. 7, 2006 entitled "Self Sealing Fenestration and Fenestration Array" the contents of which are incorporated in their entirety herein and for all purposes.

TECHNICAL FIELD

This invention relates to a medical device and more particularly to a stent graft deployed by endovascular techniques.

BACKGROUND OF THE INVENTION

Stent grafts have been proposed to provide endovascular repair of vessels of the human or animal body such as the aorta and where such a vessel includes a side branch it has been proposed to use fenestrations to allow fluid access to the side branch. It is difficult, however, to align a stent graft with a fenestration to a side branch when deploying the stent graft by endovascular techniques.

Once such example is the thoracic arch of a patient where three main vessels exit from the thoracic arch and if a stent graft is to be deployed in such a region then fenestrations are required to allow access to these side branches.

It would be an advantage if there were a number of fenestrations so that the closest to a side branch could be used but the unused fenestrations could provide sealing problems.

It is the object of this invention to provided a stent graft arrangement for such a situation.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form the invention is said to reside in a fenestration for a stent graft, the stent graft comprising a body of a biocompatible graft material and the fenestration comprising an aperture in the biocompatible graft material and at least one flap, the at least one flap comprising a biocompatible graft material, the or each flap extending across the aperture whereby to close off the aperture, wherein the or each flap can be displaced to allow access through the fenestration.

Preferably the or each flap is fastened to the biocompatible graft material of the stent graft around a part of the periphery of the aperture such that it or they can be displaced to allow access through the fenestration.

In one embodiment the fenestration can comprise two flaps, a first flap extending from one side of the aperture and a second flap extending from an opposite side of the aperture and the first and second flaps overlapping and being on the same side of the body of the biocompatible graft material.

The flaps can include a resilient reinforcement whereby to hold the flap or flaps in a sealing position over the aperture. Such a resilient reinforcement can comprise an arcuate portion of a shape memory wire.

There can be two flaps, a first flap extending from one side of the aperture and a second flap extending from an opposite side of the aperture and the first and second flaps overlapping and being on the same side of the body of the biocompatible graft material and at least one thread fastened through the flaps and into a releasable slip knot and holding the first and second flaps together in a sealing position over the aperture. The slip knot or knots can be opened by passing a guide wire between the flaps and then forcing a dilator over the guide wire and between the flaps.

The aperture can include a resilient peripheral ring formed for instance from a shape memory wire and stitched to the periphery of the aperture. The resilient ring could also be a resilient band or a continuous wire or any other similar material. However, the resilient reinforcements need not to be very strong as blood pressure will assist in holding the flap closed over the aperture and the reinforcement are merely needed to ensure that the flap remains over the fenestration until access is required.

Preferably the or each flap is inside of the fenestration whereby blood pressure within the stent graft engages against the flap or flaps and assists in sealing its or their edges against the periphery of the aperture thereby sealing the aperture.

In an alternative embodiment the fenestration can comprise two flaps, a first flap extending from one side of the aperture and a second flap extending from an opposite side of the aperture and the first and second flaps overlapping to define an inner flap and an outer flap and a resilient reinforcement associated with the outer flap whereby to hold the outer flap and thereby the inner flap in a sealing position over the aperture. The outer flap is that flap which is more outermost when viewed from that side of the fenestration upon which the flaps are mounted.

The inner flap can include an edge with at least one raised portion whereby to assist with engagement of a guide wire between the inner and outer flaps to assist with catheterisation of the fenestration. The inner flap is that flap whose edge across the fenestration can be viewed from the outside the stent graft.

In an alternative form the invention comprises a stent graft comprising a tubular body of a biocompatible graft material, a plurality of stents attached to and supporting the tubular body and at least one fenestration in the tubular body, the fenestration comprising an aperture in the tubular body and at least one flap of a biocompatible graft material covering the aperture whereby the flap closes off the aperture but can be displaced to allow access through the fenestration.

Preferably the or each flap is fastened to the biocompatible graft material of the stent graft around a part of the periphery of the aperture.

In one embodiment the fenestration in the stent graft can comprise two flaps, a first flap extending from one side of the aperture and a second flap extending from an opposite side of the aperture and the first and second flaps overlapping and being on the same side of the body of the biocompatible graft material.

The flaps can include a resilient reinforcement whereby to hold the flap or flaps in a sealing position over the aperture. Such a resilient reinforcement can comprise an arcuate portion of a shape memory wire.

And the fenestration can also include at least one thread fastened through the flaps and into a releasable slip knot and holding the first and second flaps together in a sealing position over the aperture. The slip knot or knots can be opened by passing a guide wire between the flaps and then forcing a dilator over the guide wire and between the flaps.

The aperture can include a resilient peripheral ring formed for instance from a shape memory wire. The resilient ring could also be a resilient band or a continuous wire or any other similar material. However, the resilient reinforcements need not to be very strong as blood pressure will assist in holding the flap closed over the aperture and the reinforcement are merely needed to ensure that the flap remains over the fenestration until access is required.

Preferably the or each flap is inside of the fenestration whereby blood pressure within the stent graft engages against the flap or flaps and assists in sealing its or their edges against the periphery of the aperture thereby sealing the aperture.

In an alternative form the invention comprises a stent graft comprising a tubular body of a biocompatible graft material, a plurality of stents attached to and supporting the tubular body and a plurality of fenestrations in a selected array on a portion of the tubular body, each fenestration comprising an aperture in the tubular body and at least one flap of a biocompatible graft material covering the aperture whereby the flap closes off the aperture but can be displaced to allow access through the fenestration.

The selected array of fenestrations on the portion of the tubular body can comprise one to three fenestrations wide and one to six fenestrations long.

In an alternative form the invention comprises a stent graft for deployment into the thoracic arch of a patient, the stent graft comprising a tubular body of a biocompatible graft material defining in use an arcuate tube comprising an outer curved side, a plurality of stents attached to and supporting the tubular body and a plurality of fenestrations in a selected array on the outer curved side of the tubular body, each fenestration comprising an aperture in the tubular body and at least one flap of a biocompatible graft material covering the aperture whereby the flap closes off the aperture but can be displaced to allow access through the fenestration. Each of the fenestrations can be as discussed above.

The selected array of fenestrations on the outer curved side of the tubular body comprises one to three fenestrations wide and one to six fenestrations long.

It will be seen that by this arrangement it is provided one or a plurality of fenestrations in an array on a stent graft which, when the stent graft is deployed into the vasculature of a patient, is or are sealed because the flap or flaps extends over the or each fenestration but the flap or flaps can be opened by engagement of the fenestration from the outer side of the tubular graft body through the side branch vessel and by this arrangement the flap can be opened and a side arm stent graft deployed through the fenestration into the side arm.

Where there are multiple side branch vessels such as discussed above in relation to the thoracic arch then a guide wire deployed by Seldinger techniques into the side vessel and advanced towards the thoracic arch can be used to access the closest of the fenestrations to the respective side branch and other fenestrations which are not used in the stent graft will remain sealed. It may be noted that generally there is enough flexibility between a side vessel and the main vessel in the vasculature of a patient to enable alignment of the side vessel with a selected fenestration when an extension leg is placed into the fenestration from the side vessel.

BRIEF DESCRIPTION OF THE DRAWING

This then generally describes the invention but to assist with understanding reference will now be made to accompanying drawings which show preferred embodiments of the invention.

In the drawings.

DETAILED DESCRIPTION

Figure 1:
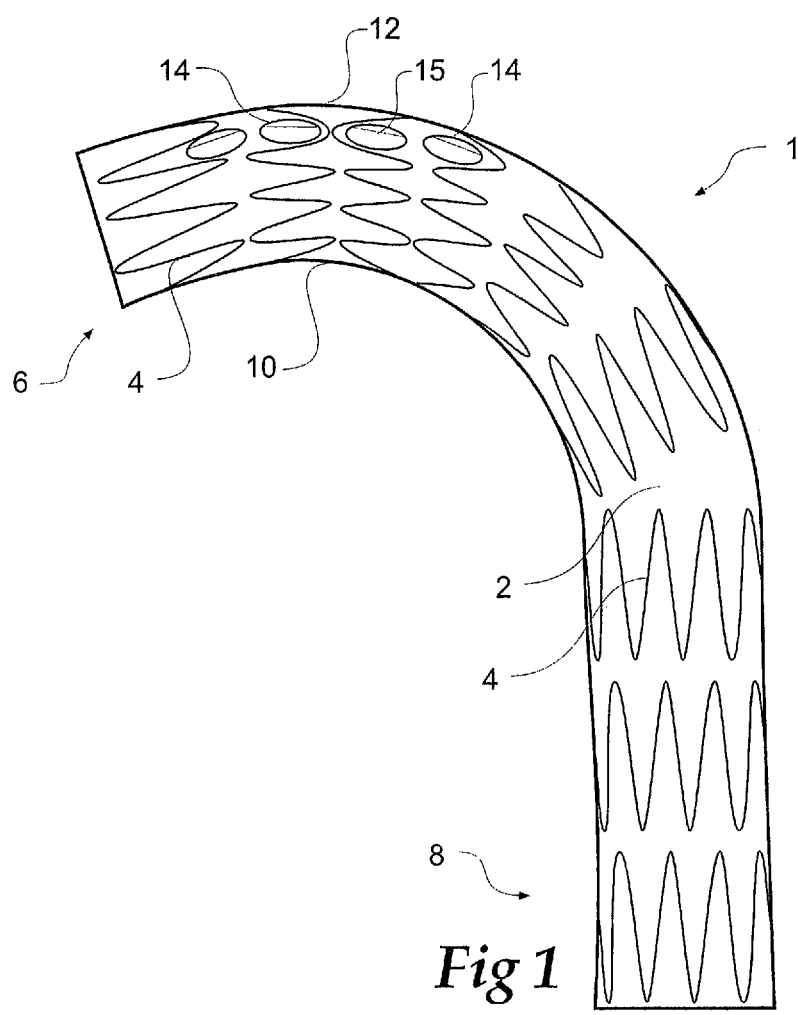
FIG. 1 shows a stent graft incorporating an array of fenestrations according to the present invention.
Figure 2:
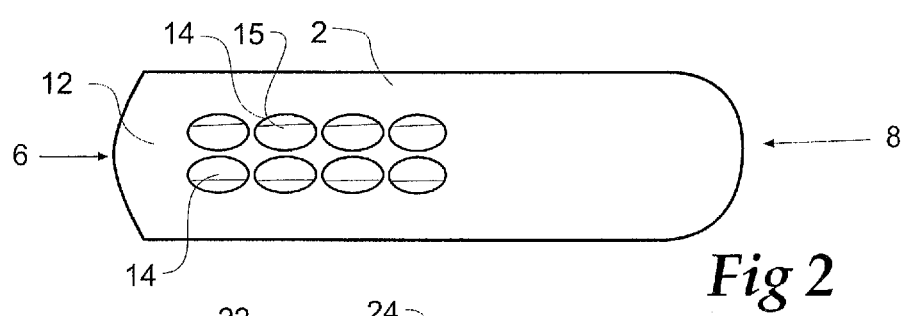
FIG. 2 shows a plan view of the stent graft shown in FIG. 1.

Now looking at the drawings and in particular FIGS. 1 and 2, a first embodiment of stent graft according to the invention is shown. FIG. 1 shows a schematic side on view and FIG. 2 shows a top view. In this embodiment the stent graft 1 comprises a tubular body 2 of a biocompatible graft material. The stent graft is intended for placement within the thoracic arch of the patient and hence is pre-curved into the shape as illustrated or is able to be curved into the shape as illustrated upon deployment. The stent graft has a plurality of stents 4 on the proximal arch portion 6 of the tubular body 2 as well as the substantially linear distal portion 8 of the tubular body 2. The arch shape defines an inner curve region 10 and an outer curve region 12. A plurality of fenestrations 14 are placed on the outer curve 12 region of the proximal end 6 of the stent graft. These fenestrations 14 are intended to substantially align with expected position of the major branch vessels of the thoracic arch of a patient. There is, however, some variation both circumferentially and longitudinally in the position of the vessels and the plurality of fenestrations allows the closest to a particular branch vessel to be used in an endovascular side branch procedure.

As can be seen in FIG. 2 there is an array of fenestrations 14 which is two fenestrations wide and four fenestrations long. Each fenestration is closed by a flap arrangement 15 as will be discussed in more detail later but can be opened by engagement against it by a guide wire or dilator using access from one of the branch vessels. In FIG. 2 the stents are omitted to assist with clarity of the understanding of the configuration.

Although an array of two fenestrations wide by four fenestrations long has been illustrated, other arrays such as three wide and three long, may also be used.

Figure 3:
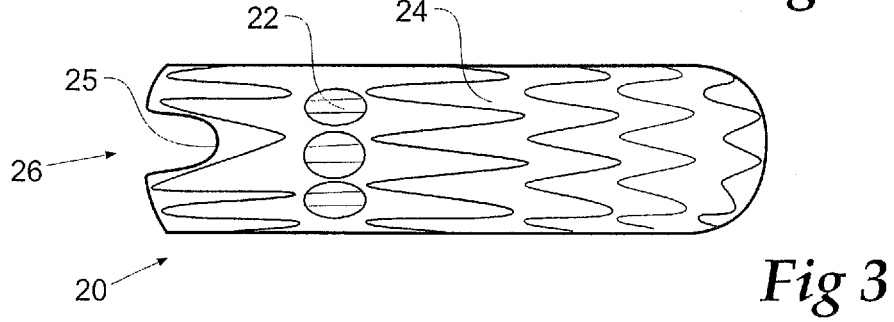
FIG. 3 shows a plan view of an alternative embodiment of the stent graft and fenestrations according to the present invention.

FIG. 3 shows an alternative embodiment of stent graft 20 suitable for the thoracic arch of a patient. The stent graft 20 is viewed in plan view. In this embodiment there are three self-sealing fenestrations 22 that are positioned on part of the circumference of the tubular body 24 on the outer curve region 12. This thoracic arch stent graft may be used where it is intended to provide a side branch connection into the left subclavian artery. The left carotid artery is not occluded because there is provided a scalloped portion 25 at the proximal end 26 of the stent graft on the outer curve 12 of the tubular body 2.

Figure 4:
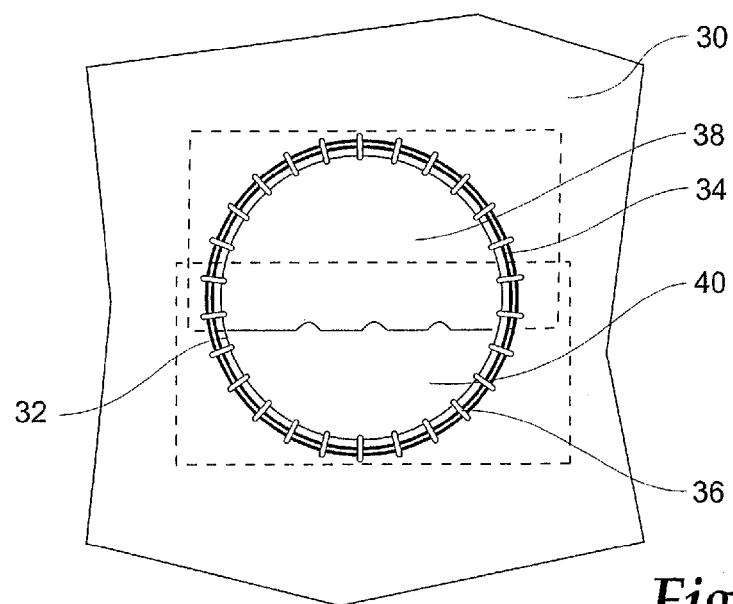
FIG. 4 shows a first embodiment of a fenestration as viewed from outside the stent graft.
Figure 5:
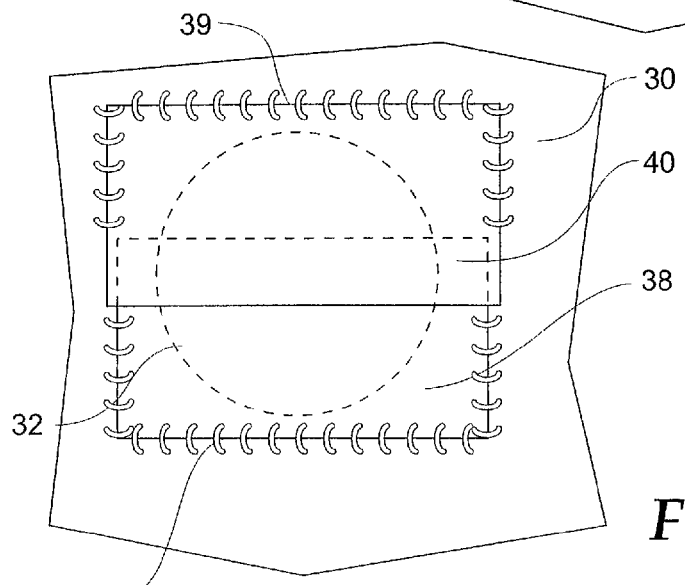
FIG. 5 shows an embodiment of FIG. 4 as viewed from the inside of the stent graft.
Figure 6:
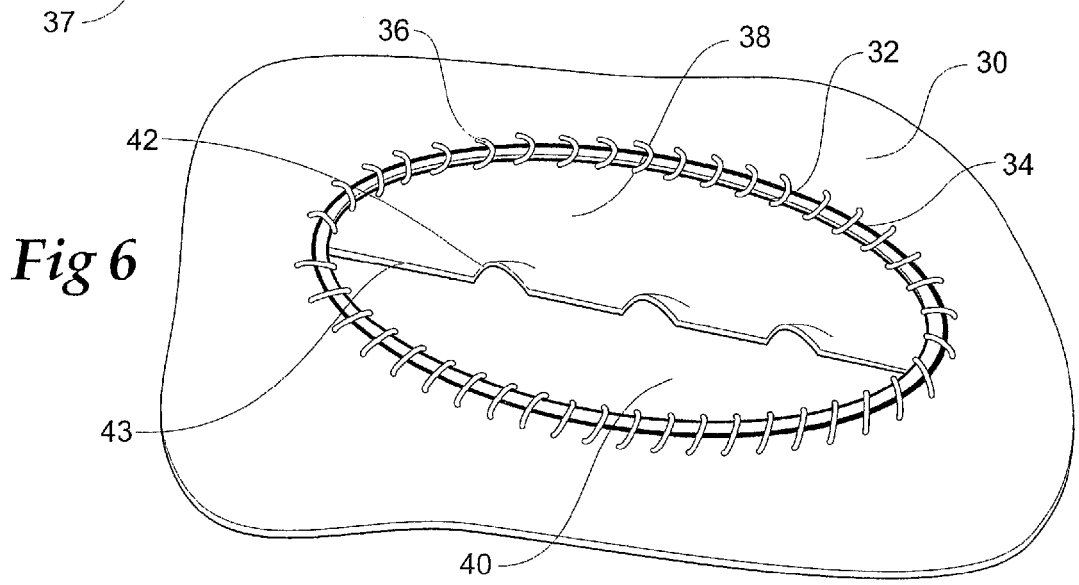
FIG. 6 shows a perspective view of the fenestration portion of a stent graft from the outside of the stent graft.

FIGS. 4, 5 and 6 show a first embodiment of a self-sealing fenestration according to the present invention. FIG. 4 shows an outside view of the fenestration, FIG. 5 shows an inside view of the fenestration and FIG. 6 shows a perspective view on the outside.

The stent graft into which the fenestration is placed is formed from a biocompatible graft material 30 with an aperture 32 forming a fenestration. The fenestration is surrounded by a reinforcing ring 34 stitched into the periphery of the aperture by means of stitching 36.

As can be seen in FIG. 5, the fenestration is closed off by first and second flaps 38 and 40 of a biocompatible graft material. Viewed from the outside in FIG. 4 the flap 38 overlaps the flap 40 and both are inside the aperture 32. Viewed in FIG. 5 the flap 40 overlaps the flap 38.

Looking at the view in FIG. 6 it will be noted that the flap 38 includes several raised portion 42 along its edge across the fenestration. These raised portion allow a point of purchase for a guide wire or dilator deployed from outside the fenestration to enable to engage against the flap and to allow access through the fenestration for placement of a branch stent graft.

It will be noted, as can be particularly seen in FIG. 5 that the flap 38 is stitched to the stent graft 30 by stitching 37 and the flap 40 is also stitched to the stent graft 30 by means of stitching 39. The stitchings 37 and 39 extends around part of the flaps but leave a central portion not stitched so the flaps can be opened back to allow access through the fenestration.

Figure 7:
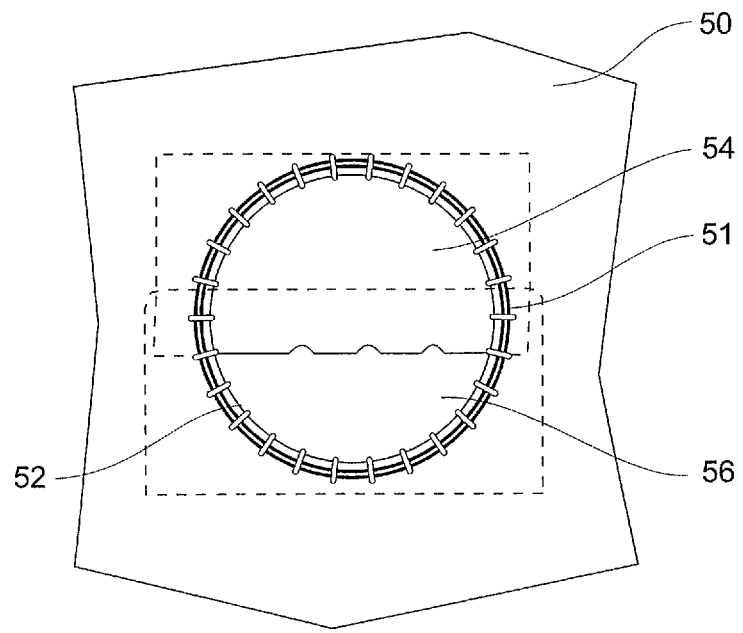
FIG. 7 shows an alternative embodiment of fenestration on a stent graft as viewed from the outside of a stent graft.
Figure 8:
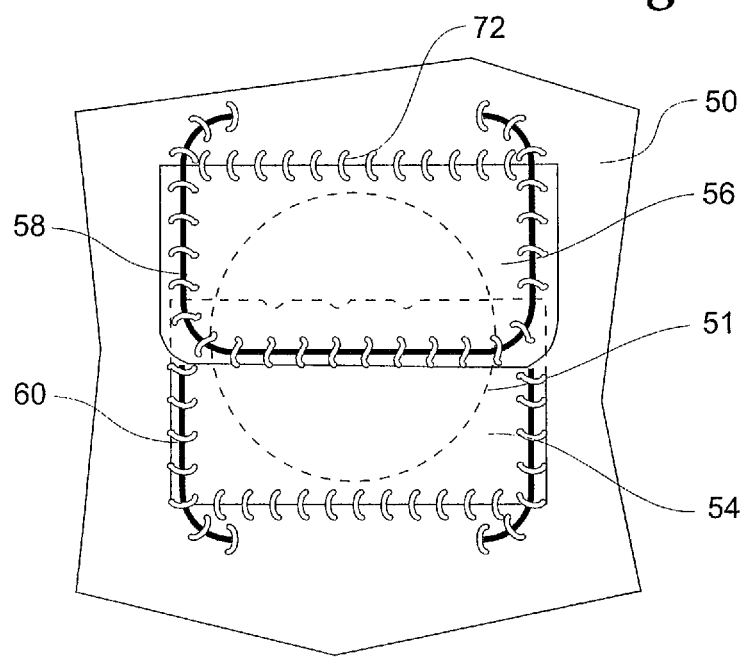
FIG. 8 shows a view of the fenestration of FIG. 7 as viewed from inside the stent graft.

FIGS. 7 and 8 show outside and inside views of an alternative embodiment of a fenestration suitable for a stent graft according to the present invention. FIG. 7 shows an outside view and FIG. 8 shows an inside view of the fenestration.

In FIG. 7 the stent graft 50 has a fenestration 52 with first flap 54 and second flap 56 stitched across the fenestration. The fenestration includes a reinforcing ring 51 around its periphery.

As can be particularly seen in FIG. 8, however, the flap 56 has a resilient reinforcement band 58 stitched or otherwise fastened to it and the flap 54 has a resilient reinforcement band 60 stitched or otherwise fastened to it. The resilient reinforcements 58 and 60 extend back onto the stent graft 50 and assist with holding the flaps 54 and 56 in a closed position over the fenestration 52. The resilient reinforcements, however, allow the flaps to be opened for access therethrough. Generally the resilient reinforcements 58 and 60 need not be very strong as blood pressure will assist in holding the flap closed over the aperture and the reinforcements are merely needed to ensure that the flap remains over the fenestration until access is required.

Figure 9:
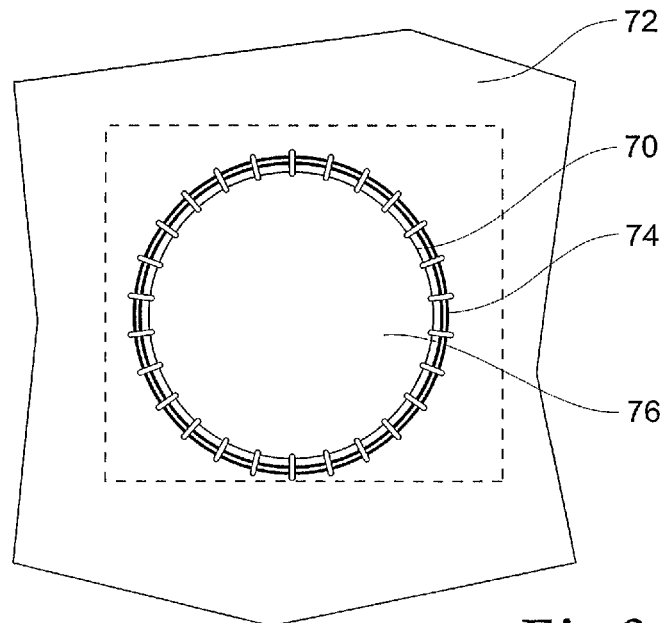
FIG. 9 shows a still further embodiment of fenestration according to the present invention as viewed from the outside of a stent graft.
Figure 10:
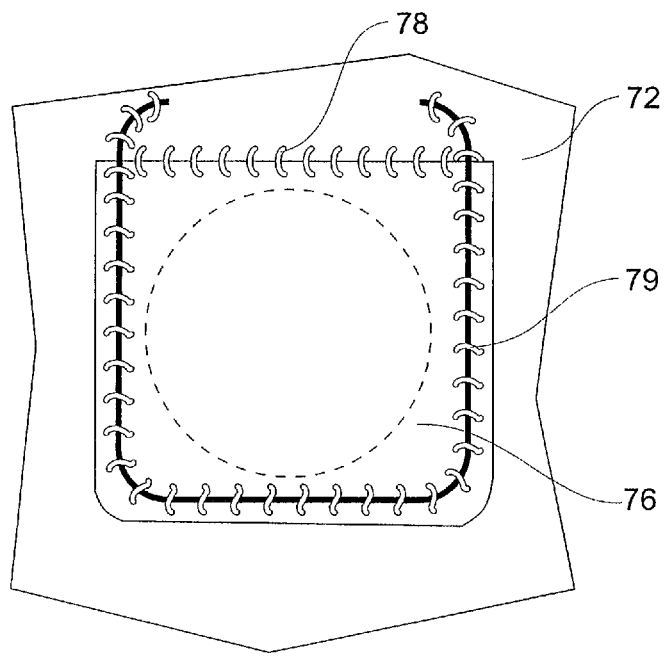
FIG. 10 shows a view of the fenestration of FIG. 9 as viewed from inside the stent graft.

FIGS. 9 and 10 show an alternative an embodiment of fenestration arrangement of the present invention. FIG. 9 shows an outside view and FIG. 10 shows an inside view of the fenestration.

The fenestration 70 in the stent graft 72 includes a resilient reinforcement ring 74 around the periphery of the fenestration 70.

As can be seen on the inside there is a single flap 76 of a biocompatible graft material which is stitched on one side by stitching 78 and 79 and is held across the fenestration by means of a resilient reinforcement which is stitched by stitching around three sides of the flap then than back into the stent graft 72.

Once again this flap can be lifted by access from the outside to allow access through the fenestration.

Generally the resilient reinforcement ring 74 need not be very strong as blood pressure will assist in holding the flap closed over the aperture and the reinforcement is merely needed to ensure that the flap remains over the fenestration.

Figure 11:
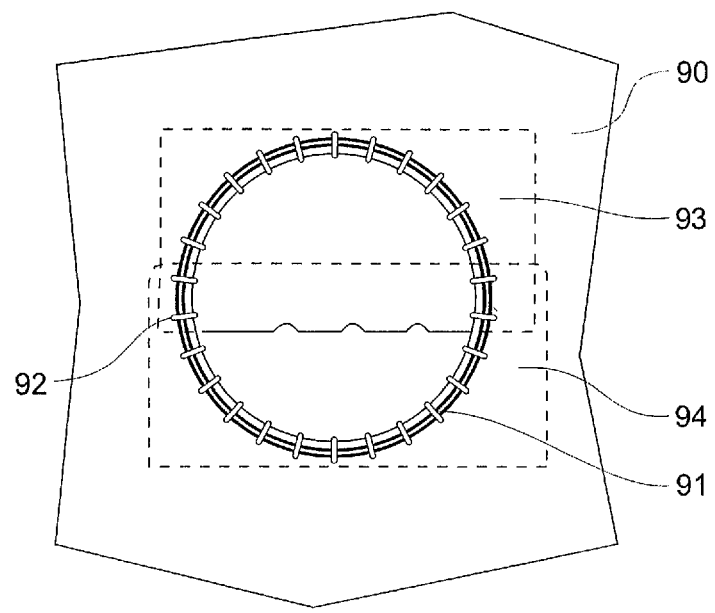
FIG. 11 shows a still further embodiment of a stent graft according to the present invention including a fenestration as viewed from outside the stent graft.
Figure 12:
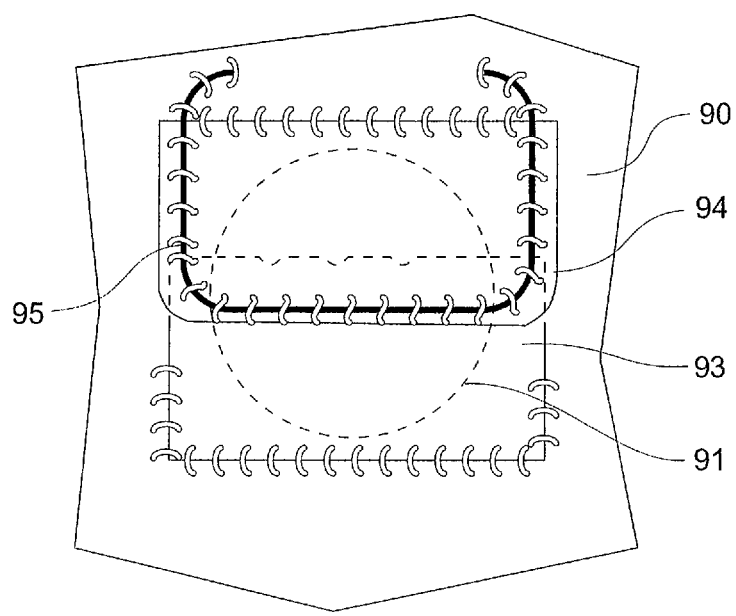
FIG. 12 shows the embodiment of FIG. 11 as viewed from the inside of the stent graft.

FIGS. 11 and 12 show still a further embodiment of a fenestration for a stent graft according to the present invention. FIG. 11 shows a fenestration as viewed from outside the stent graft and FIG. 12 as viewed from the inside of the stent graft. In this embodiment the stent graft material 90 has a fenestration 91 defined by a peripheral reinforcing ring 92. There are two flaps 93 and 94 on the inside of the stent graft body with the flap 93 being on the outside of the flap 94 as viewed from outside the stent graft.

As can be seen in FIG. 12 in this embodiment there is a resilient reinforcement 95 stitched to the flap 94 on the inside of the stent graft but no resilient reinforcement on the flap 93. The flap 94, however, overlaps the flap 93 on the inside and holds it in place to ensure sealing of the aperture.

Figures 13, 14:
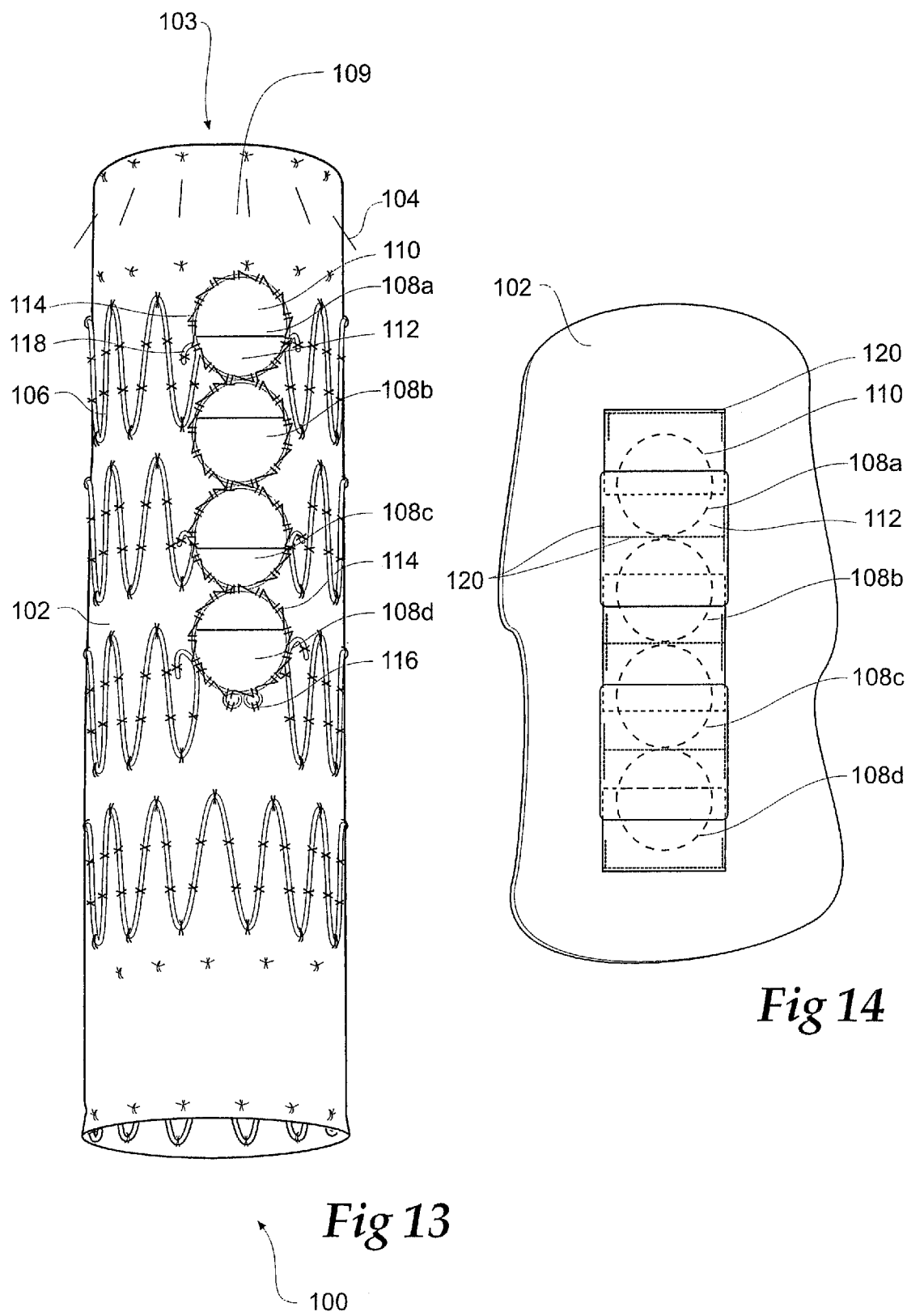
FIG. 13 shows an alternative embodiment of stent graft incorporating an array of fenestrations according to the present invention.
FIG. 14 shows a detail of the embodiment of FIG. 13 as viewed from the inside of the stent graft.

FIG. 13 shows an alternative embodiment of a stent graft incorporating an array of fenestrations according to the present invention and FIG. 14 shows a detail of the embodiment of FIG. 13 as viewed from the inside of the stent graft.

The stent graft 100 has a tubular body 102 with barbs 104 at the proximal end 103 to provide good fixation into the thoracic arch of a patient. The tubular body 102 includes a plurality of stents 106 along its length to provide support for the tubular body. A plurality of fenestrations 108a, 108b, 108c and 108d are provided on the side 109 which will be on the outer curve of the stent graft when it is deployed into the thoracic arch of a patient.

Each fenestration 108a, 108b, 108c and 108d is defined by a reinforcing ring formed by a continuous resilient wire 114 in a figure eight arrangement around the four fenestrations and terminating in loops 116 adjacent to fenestration 108d. Where a fenestration 108a, 108b, 108c and 108d interrupts a stent 106 the stent is cut and the cut ends are curved into a loop 118 so that the sharp end does not present a point which could damage the vasculature. The curved cut end 118 is also stitched to the continuous resilient wire 114 to provide some structural integrity to the stent and ring.

Each fenestration 108 is covered on the inside as can be particularly seen in FIG. 14 by a pair of flaps 110, 112 which overlap to provide a seal. The flaps 110 and 112 cover the fenestration 108a and the flap 112 also covers part of the fenestration 108b. The flaps are stitched onto the tubular body 102 by stitching 120 around part of their periphery to hold them on place but so that they can be displaced as necessary to provide access through the fenestration.

Figure 15:
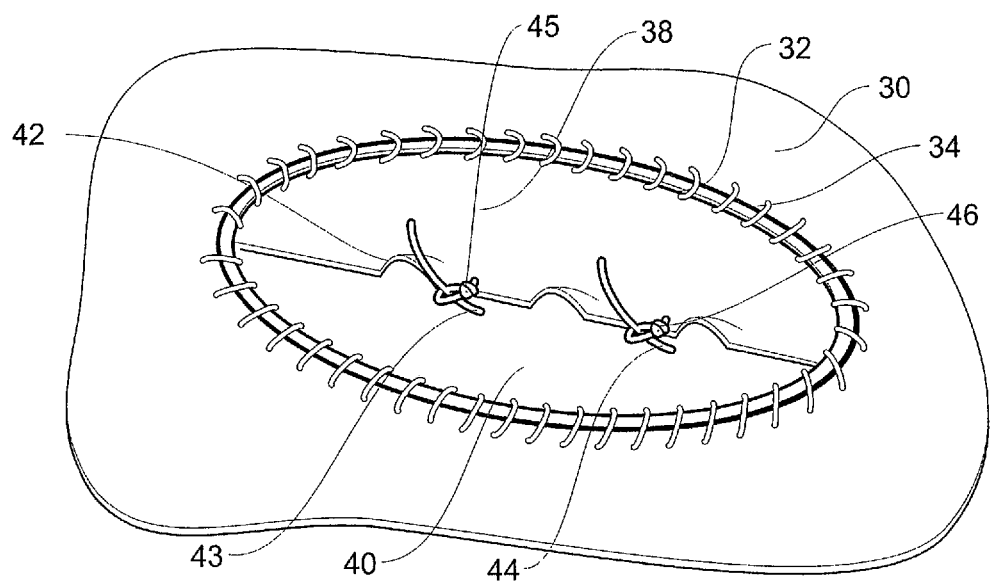
FIG. 15 shows a still further embodiment of fenestration incorporating a slip knot according to the present invention as viewed from the outside of a stent graft.
Figure 16:
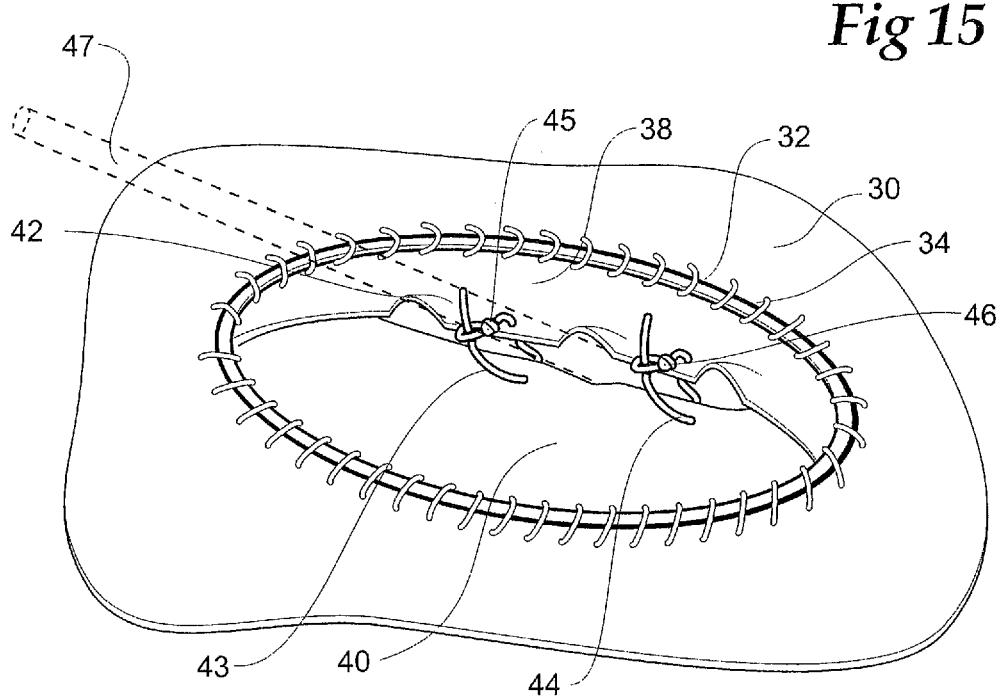
FIG. 16 shows the embodiment of fenestration shown in FIG. 15 with a guide wire through the fenestration.

FIG. 15 shows a still further embodiment of fenestration incorporating a slip knot according to the present invention as viewed from the outside of a stent graft and FIG. 16 shows the embodiment of fenestration shown in FIG. 15 with a guide wire through the fenestration, again viewed from outside the stent graft. This embodiment is similar to that shown in FIG. 6 and the same reference numeral are used for corresponding items.

FIG. 15 shows a perspective view on the outside of a stent graft incorporating a fenestration. The stent graft 30 into which the fenestration is placed is formed from a biocompatible graft material with an aperture 32 forming a fenestration. The fenestration is surrounded by a reinforcing ring 34 stitched in by means of stitching 36. The fenestration is closed off by first and second flaps 38 and 40 of a biocompatible graft material which overlap. Viewed from the outside the flap 38 overlaps the flap 40 and both are inside the aperture 32. It will be noted that the flap 38 includes several raised portion 42 along its edge across the fenestration. These raised portion allow a point of purchase for a guide wire or dilator deployed from outside the fenestration to enable it to engage against the flap and to allow access through the fenestration for placement of a branch stent graft.

The two flaps 38 and 40 are held closed partially by blood pressure engaging against the flaps from inside and assisted by the overlap and also by sutures 43 and 44 which are each stitched through the flaps and tied with slip knots 45 and 46. The slip knots 45 and 46 are formed so as to slip when the two portions of flap material through which they are stitched are forced apart. As can be seen in FIG. 16, when a guide wire or dilator 47 (shown dotted) is deployed to engage with a selected fenestration of an array of fenestrations and it is passed between the flaps 38 and 40 the slip knot can slip to allow access. Deploying a dilator over the guide wire to continue to open the flaps will cause the slip knots to loosen and eventually to release. The sutures 43 and 44 are connected to the flap 38 so when the slip knot releases the suture does not become free.

Generally it will be seen by the various embodiments of this invention there is shown a fenestration arrangement which has at least one flap across it to ensure that the fenestration is sealed at least by the use of blood pressure which engages against the flaps and causes their edges to seal around the periphery of the aperture and optionally some resilient assistance to hold the flap in position but can be opened to allow access through the fenestration for placement on the leg extension during an endovascular procedure.

Throughout this specification various indications have been given as to the scope of the invention but invention is not limited to any one of these but may reside in two or more of these combined together. The examples are given for illustration only and not for limitation.

The invention claimed is:

1. A stent graft comprising at least one fenestration, the stent graft being for deployment into vessels of the human or animal body the stent graft comprising a tubular body of a biocompatible graft material, a plurality of stents attached to and supporting the tubular body, the or each fenestration comprising an aperture in the biocompatible graft material and two flaps, the two flaps comprising a biocompatible graft material, the aperture comprising a first side and a second side and an inner side and an outer side, the inner side being within the tubular body, the two flaps extending across the aperture on the inner side of the aperture whereby to close off the aperture, the two flaps comprising a first flap extending from the first side of the aperture and a second flap extending from the second side of the aperture and the first and second flaps overlapping each other to define an inner flap and an outer flap with the inner flap overlapping the outer flap when viewed from within the tubular body and a resilient reinforcement associated with the inner flap whereby to hold the inner flap and thereby the outer flap in a sealing position over the aperture, wherein the two flaps can be displaced to allow access through the fenestration.

2. The stent graft as in claim 1 wherein the two flaps are each fastened to the biocompatible graft material of the stent graft around a part of the periphery of the aperture.

3. The stent graft as in claim 1 wherein each flap includes a resilient reinforcement whereby to hold the first flap and the second flap in a sealing position over the aperture.

4. The stent graft as in claim 1 wherein the resilient reinforcement comprises an arcuate portion of a shape memory wire.

5. The stent graft as in claim 1 comprising at least one thread fastened through the first flap and the second flap and a slip knot in the thread thereby holding the first and second flaps together in a sealing position over the aperture, the slip knot being released when the two portions of flap material through which they are stitched are forced apart.

6. The stent graft as in claim 1 wherein the or each aperture includes a resilient peripheral ring.

7. The stent graft as in claim 1 wherein the outer flap includes an edge with a raised portion whereby to assist with engagement of a guide wire between the inner and outer flaps to assist with displacement of the flaps and catheterisation of the fenestration.

8. A fenestration in a stent graft, the fenestration comprising aperture and a peripheral reinforcing ring around the aperture and two flaps, the two flaps comprising a biocompatible graft material, the aperture comprising a first side and a second side and an inner side and an outer side, the two flaps extending across the aperture on the inner side of the aperture whereby to close off the aperture, the two flaps comprising a first flap extending from the first side of the aperture and a second flap extending from the second side of the aperture and the first and second flaps overlapping each other to define an inner flap and an outer flap with the inner flap overlapping the outer flap and a resilient reinforcement associated with the inner flap whereby to hold the inner flap and thereby the outer flap in a sealing position over the aperture, wherein the two flaps can be displaced to allow access through the fenestration.

9. The stent graft as in claim 8 wherein each flap includes a resilient reinforcement whereby to hold the first flap and the second flap in a sealing position over the aperture.

10. The stent graft as in claim 8 wherein the resilient reinforcement comprises an arcuate portion of a shape memory wire.

11. The stent graft as in claim 8 comprising at least one thread fastened through the first flap and the second flap and a slip knot in the thread thereby holding the first and second flaps together in a sealing position over the aperture, the slip knot being released when the two portions of flap material through which they are stitched are forced apart.

12. The stent graft as in claim 8 wherein the outer flap includes an edge with a raised portion whereby to assist with engagement of a guide wire between the inner and outer flaps to assist with displacement of the flaps and catheterisation of the fenestration.

* * * * *